(12) United States Patent
Amon

(10) Patent No.: US 8,517,026 B2
(45) Date of Patent: Aug. 27, 2013

(54) NASAL INSERTS

(76) Inventor: Adva Beck Amon, Zichron Ya'acov (IL)

( * ) Notice: Subject to any disclaimer, the term of this patent is extended or adjusted under 35 U.S.C. 154(b) by 1041 days.

(21) Appl. No.: 12/390,893

(22) Filed: Feb. 23, 2009

(65) Prior Publication Data

US 2009/0250067 A1    Oct. 8, 2009

Related U.S. Application Data

(60) Provisional application No. 61/031,175, filed on Feb. 25, 2008.

(51) Int. Cl.
*A61M 15/08* (2006.01)

(52) U.S. Cl.
USPC ............. 128/207.18; 128/200.24; 128/207.13

(58) Field of Classification Search
USPC ............. 128/200.24, 206.11, 207.13, 207.18, 128/200.26; 600/199
See application file for complete search history.

(56) References Cited

U.S. PATENT DOCUMENTS

| | | | |
|---|---|---|---|
| 2,274,997 A | 3/1942 | Thurman | |
| 2,924,217 A | 2/1960 | Regel et al. | |
| 3,145,711 A | 8/1964 | Beber | |
| 3,463,149 A | 8/1969 | Albu | |
| 4,267,831 A | 5/1981 | Aguilar | |
| 4,573,461 A | 3/1986 | Lake | |
| 4,887,597 A | 12/1989 | Holland | |
| 4,984,302 A | 1/1991 | Lincoln | |
| 5,117,820 A | 6/1992 | Robitaille | |
| 5,395,309 A | 3/1995 | Tanaka et al. | |
| 5,568,808 A | 10/1996 | Rimkus | |
| 5,601,594 A | 2/1997 | Best | |
| 5,947,119 A | 9/1999 | Reznick | |
| 6,004,342 A | 12/1999 | Filis | |
| 6,015,425 A | 1/2000 | Altadonna, Jr. | |
| 6,216,694 B1 | 4/2001 | Chen | |
| 6,484,725 B1 | 11/2002 | Chi | |
| 6,561,188 B1 | 5/2003 | Ellis | |
| 6,971,387 B2 | 12/2005 | Michaels | |
| 6,981,502 B2 | 1/2006 | McCormick et al. | |
| 7,108,198 B2 | 9/2006 | Altadonna, Jr. | |
| 7,156,098 B2 | 1/2007 | Dolezal et al. | |
| 7,156,099 B1 | 1/2007 | Jenkins | |
| 2002/0153007 A1 | 10/2002 | Davi | |
| 2002/0177871 A1 | 11/2002 | Santin | |
| 2003/0094178 A1 | 5/2003 | McAuley et al. | |
| 2003/0209145 A1 | 11/2003 | Soper | |
| 2005/0037031 A1 | 2/2005 | Jackson | |
| 2005/0211254 A1 | 9/2005 | Olson | |
| 2005/0279351 A1 | 12/2005 | Lewis et al. | |
| 2006/0272640 A1 | 12/2006 | Abullon | |
| 2006/0292254 A1 | 12/2006 | More | |
| 2007/0062538 A1 | 3/2007 | Foggia et al. | |

*Primary Examiner* — Glenn Richman
(74) *Attorney, Agent, or Firm* — The Webb Law Firm

(57) ABSTRACT

An odor preventing nasal insert and method of insertion into a nasal cavity to prevent odors from reaching the olfactory region by directing them to bypass the olfactory region, thereby decreasing impulse eating and flattening the eating experience. The nasal insert comprises a body having an inner surface which defines an air passageway surrounded by an outer surface of soft, flexible material. The nasal insert body can have a first portion and a second portion where the outer surface of said nasal insert body is configured to form a seal between the nasal insert body and the nasal cavity. The nasal insert body further includes any number sealing members extending from the outer surface of the nasal insert body, where the sealing members are adapted to the nasal cavity and can prevent air flow between the nasal insert body and the nasal cavity.

44 Claims, 11 Drawing Sheets

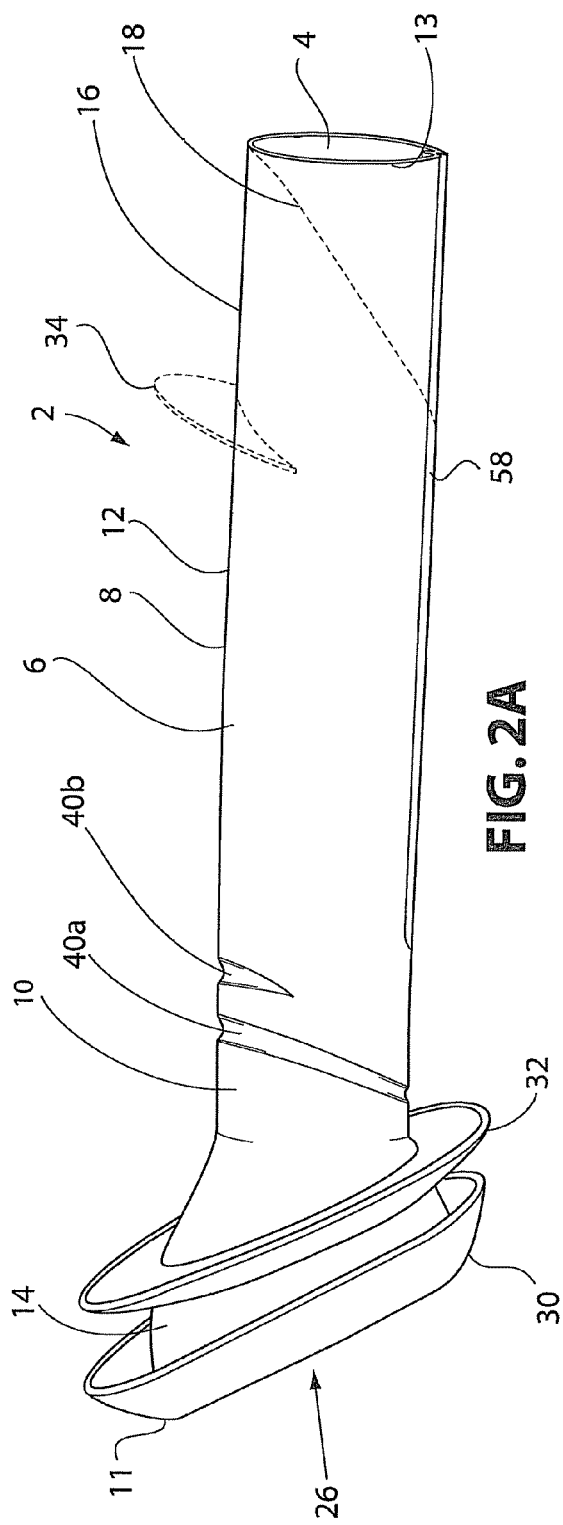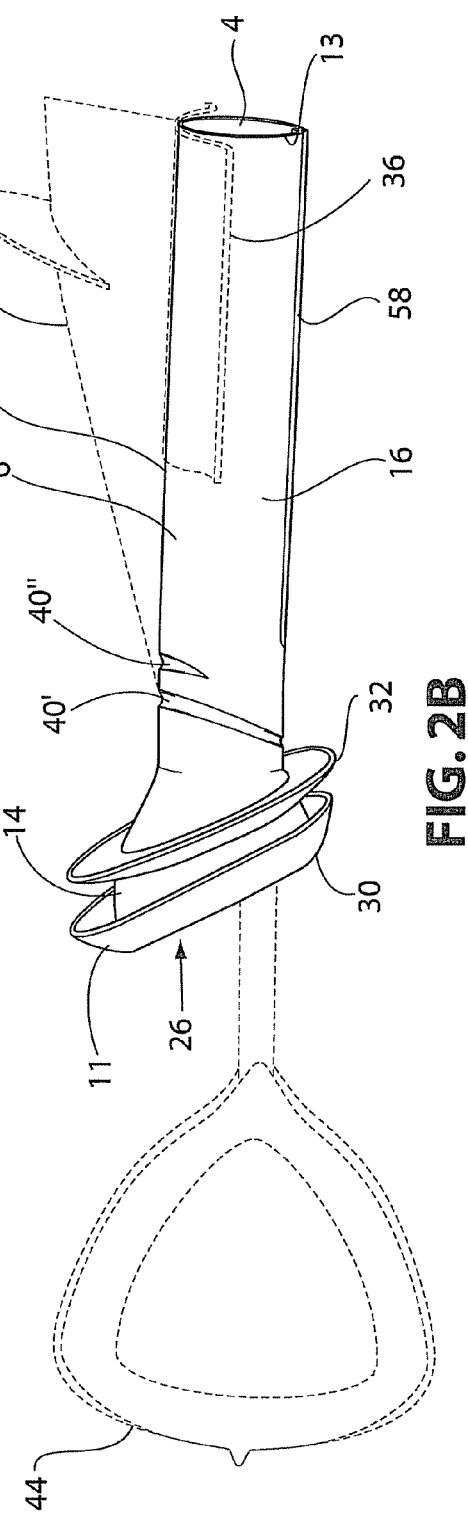

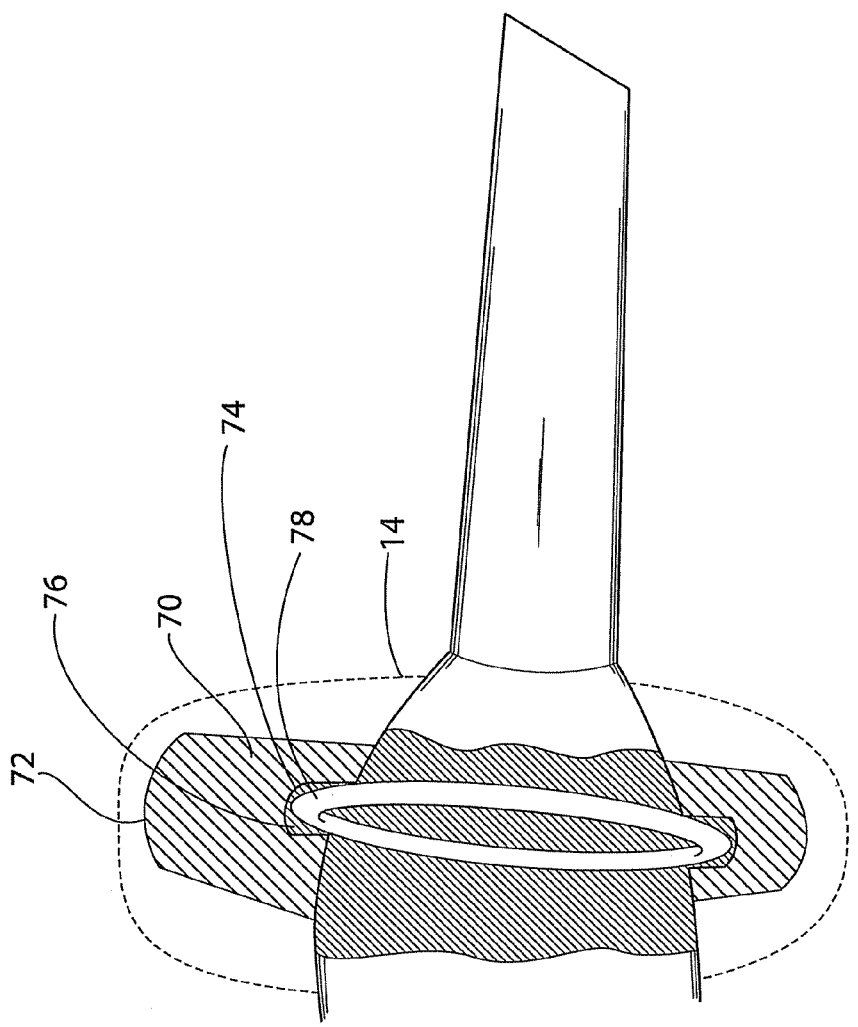

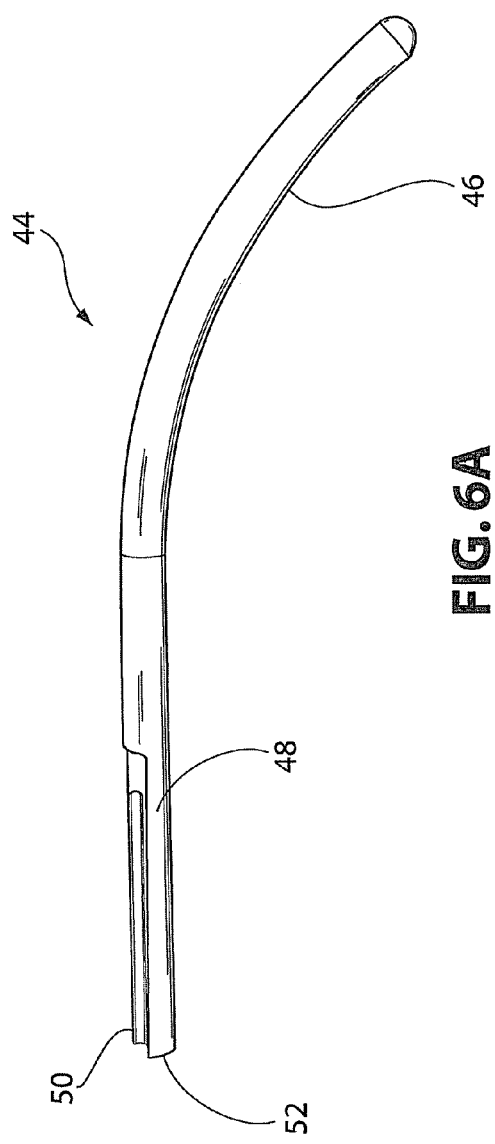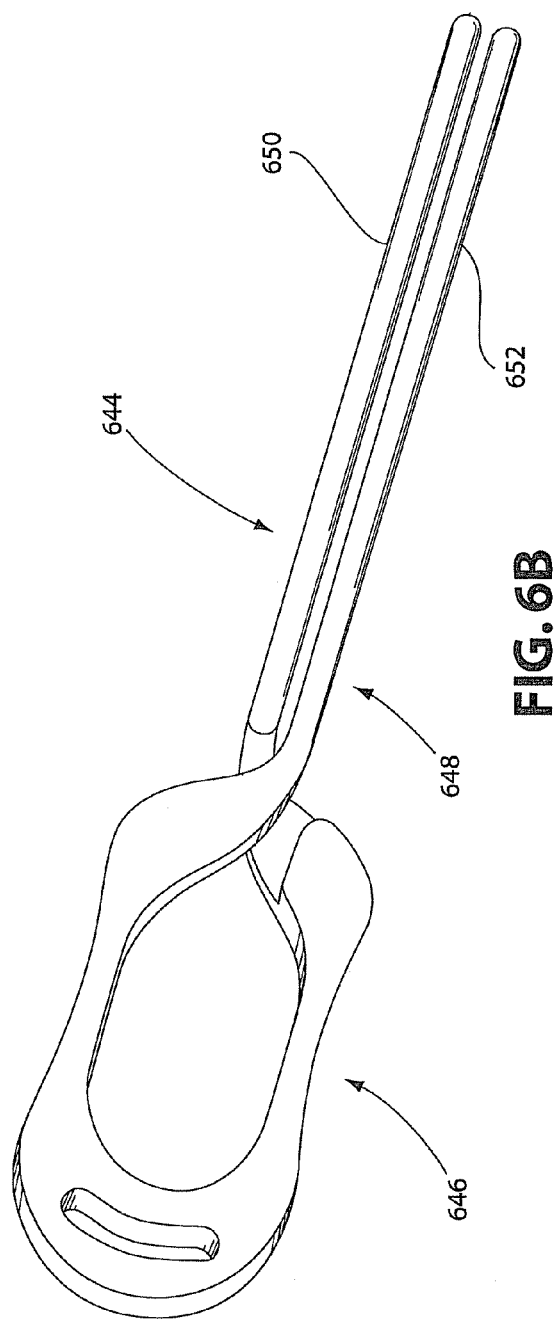
FIG. 6A
FIG. 6B

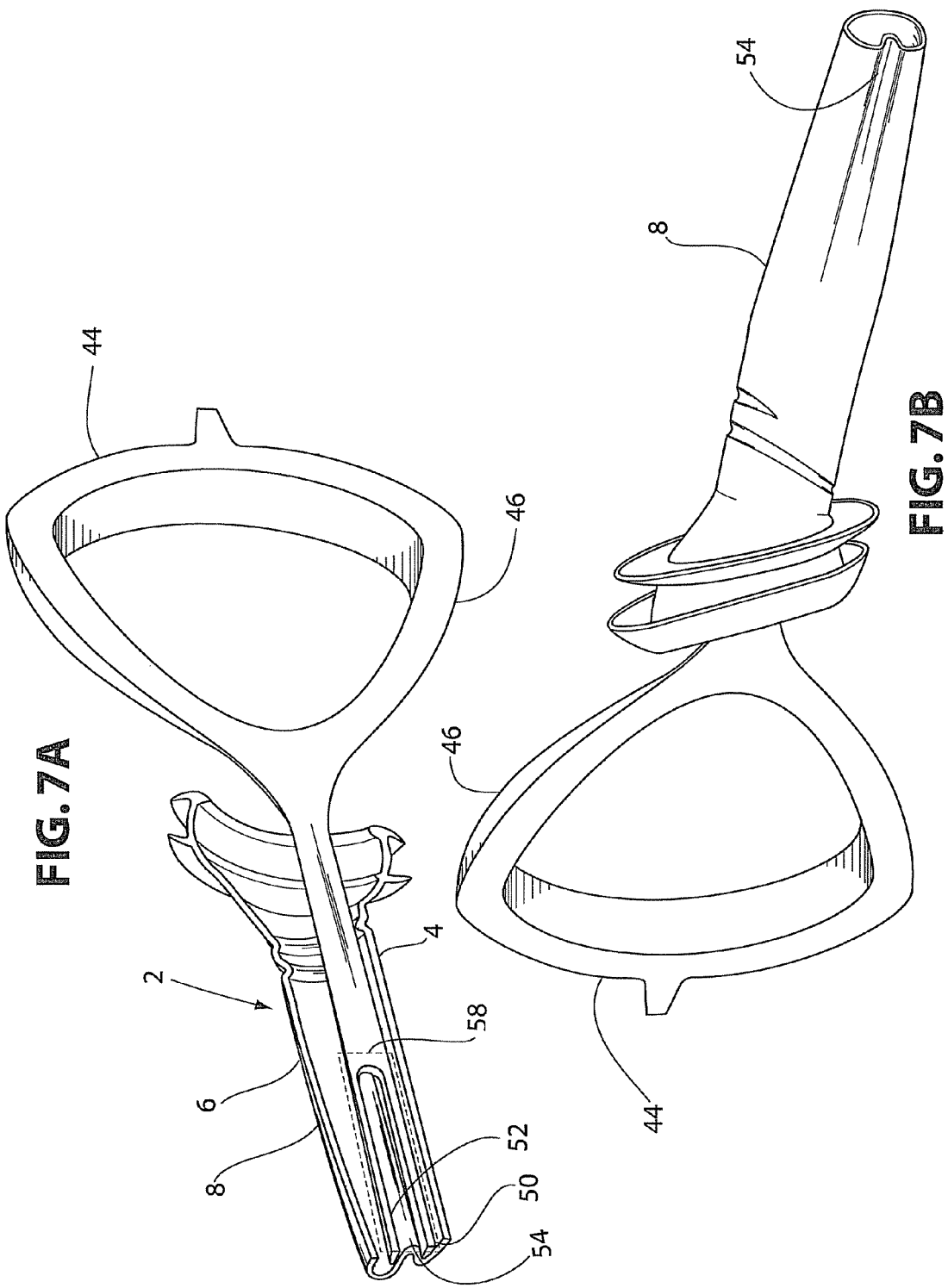

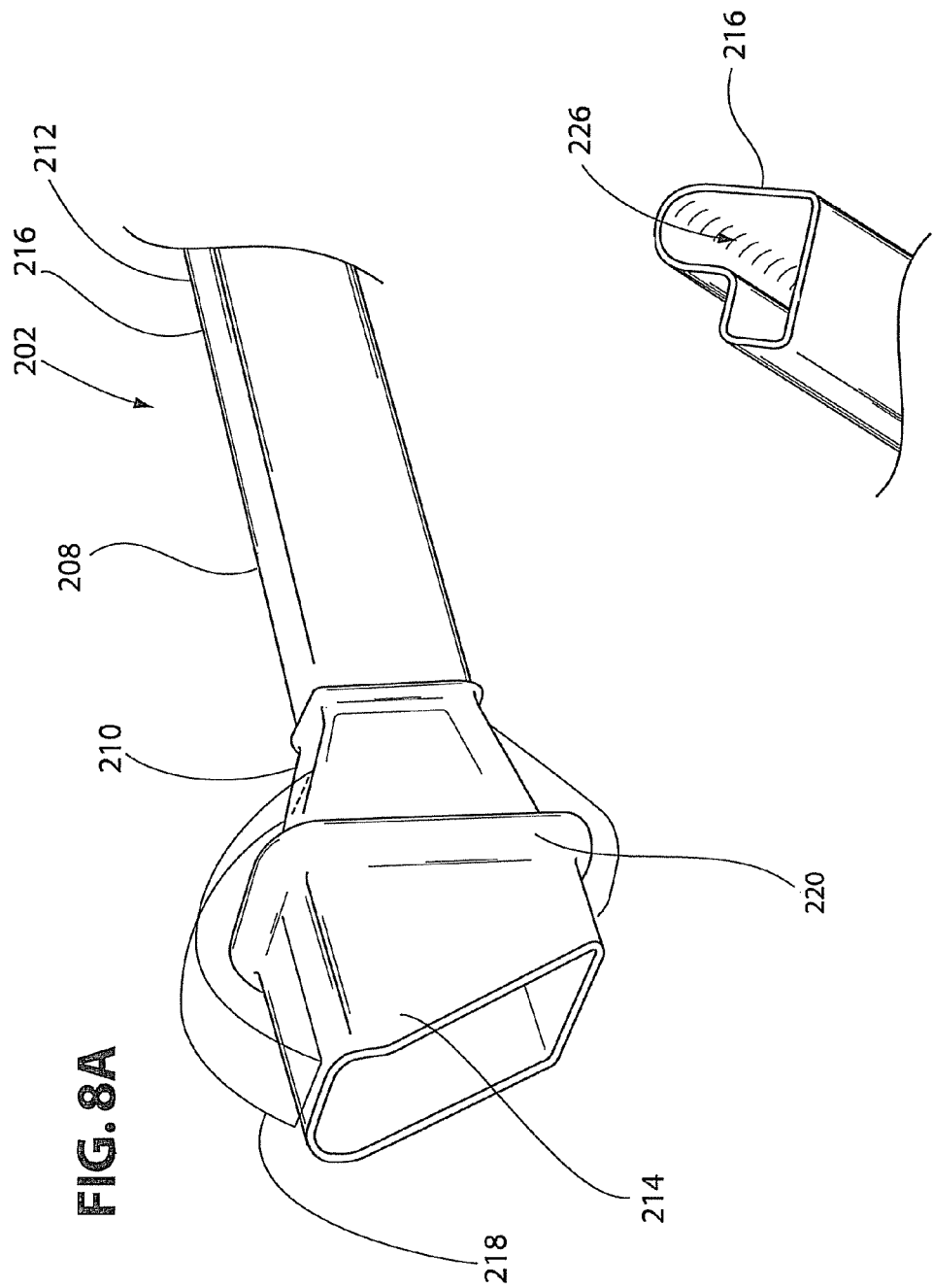

NASAL INSERTS

CROSS REFERENCE TO RELATED APPLICATIONS

This application claims the benefit of U.S. Provisional Application No. 61/031,175 entitled "Nostril inserts," filed on Feb. 25, 2008, which is hereby incorporated by reference.

BACKGROUND OF THE INVENTION

Field of the Invention

The present invention relates generally to nasal inserts and, more particularly, to a method and apparatus for decreasing food consumption by suppressing impulse eating and by flattening the eating experience. Human obesity is among the most common health and aesthetic concerns of the modern world. Overweight persons subsequently are prone to many diseases. There exist many diet systems to aide in controlling and losing weight, such as low fat and low carb diets, diet foods, and supplements such as beverages and energy pills, diuretic pills, and medicines. In addition, other more extreme methods such as stomach stapling, surgical shortening of the intestine, or fat removal are also possible.

It is known that taste and odor are physiologically interdependent, and distinct flavors are produced by aromas stimulating olfactory chemo receptors in the olfactory region of the nasal cavity. The basic taste of food is perceived by gustatory papillae in the oral cavity and throat, but this sensation is limited to sweet, bitter, sour, and salty in addition to other parameters such as temperature and texture. More complex and pleasant flavors can only be elaborated by smelling odorous particles from the object and having the odorous particles come in contact with the olfactory region of the nasal cavity. Smelling is the sensation resulting from adequate stimulation of the olfactory organ.

It is also known that one reason humans consume too much food is due to the abundance of flavorful food confronted daily. Impulse eating, the instant desire to eat when confronted with food, is in many cases primarily due to the instant development of hunger triggered by the smell of desirable food. Similar to the "discount" signs that attract a shopper to make a purchase when he or she sees them while walking through a store, many people are conditioned to eat if they come in direct contact with a desired food odor. For example, smelling fried eggs, fresh baked bread, barbeque, or hot chocolate can all cause a person to become hungry. Impulse eating can be avoided or significantly reduced by neutralizing or preventing the odor of foods from reaching the olfactory region. Even weakening the odor effect can reduce the impulse to eat.

Another cause of consuming too much food is the enjoyment of tasty, flavorful food. Since the smell of food is the primary vehicle for heightening the human eating experience, many flavors such as chocolate and coffee are mainly sensed through smelling. Without odor, or with a weaker odor, the person can only recognize the four flat tastes, namely, sweet, bitter, sour, and salty. Without the odor, texture and heat can be sensed but the flavor is very difficult to distinguish. Therefore, neutralizing the sense of smell or even weakening it while a person is eating, flattens the eating experience and dramatically reduces the pleasure of eating.

SUMMARY OF THE INVENTION

An odor preventing nasal insert for insertion into a nasal cavity can prevent odors from reaching the olfactory region or significantly reduce the amount of them. The nasal insert comprising a body having an inner surface which defines an air passageway. The nasal insert body can have a first portion and a second portion where the outer surface of said nasal insert body is configured to form a seal between the nasal insert body and the nasal cavity. The nasal insert body further includes any number of convex shaped or other shaped sealing members extending outward from the outer surface of the nasal insert body, where the sealing members are adapted to the nasal cavity and can prevent air flow between the nasal insert body and the nasal cavity and thereby direct air flow through the air passageway. The sealing members can be sealing elements, sealing material or a layer of material or a specific shape of the nasal insert body. The nasal insert body can comprise a full or partial layer or layers between the inner and outer surface of the nasal insert body. The nasal insert body can be made of an absorbent material to absorb fluids. The outer surface of the nasal insert body can be adapted to drain mucous. The sealing members of the nasal insert body can be adjacent the first portion or can be adjacent the conjunction of the first and second portion or can be placed at the second portion of the nasal insert body. Any combination of placement of the sealing members can be used having a beneficial effect of blocking the air flow from the olfactory region through the nasal cavity. As the air is blocked from entering the nasal cavity and reaching the olfactory region, air enters into the air passageway.

In one aspect of the present invention, the nasal insert body can define a gripping portion. The nasal insert body can be compressed and expand anywhere along the body. The nasal insert body can further include a flexible joint, harmonica, preferably between the first and second portion of the nasal insert body. The air passageway of the nasal insert body can alternatively be filled or partially filled with a filling material, where the filling material can be porous material, absorbent material, odor absorbent material, anti-pollution material, anti-chemical pollution material, anti-biological pollution material, medicine carrying material, medicine, odor carrying material, or alternative odor material. Also, the filling material may reduce the amount of air moving through the nasal cavity while breathing and by that reduce amount of odor reaching the olfactory in general even without a seal between the nasal insert body 8 and the nasal cavity 100. The nasal insert body itself can be made of silicone, Tygon®, hydro-gels, cotton, Merocell®, silicon, polyurethanes, polyvinylchloride, dimethylpolysiloxan, silicic acid, azodiacarbonamide, reticulated foam, polyethers, polyesters, polysiloxanes, polycarbonate, polyolefins, polybutyrate, polyethylene teraphtalate (PET), Polymides, polyethylene glycol, activated carbon, biodegradable material, anti microbial agents, plastic materials, silver, bamboo, antimony, aluminum, metal materials, polymers, wood, resins, carbon based materials, carbon nanotubes (CNT), esters.

The nasal insert body can further include material having an odor, anti-bacterial, oily or watery, or medicated material.

The nasal insert body includes a first end and a second end, wherein the shape of the first end can be wider than the second end, or the shape of the second end can be wider than the first end. The shapes of the first and second end can be shortened, slanted, curved, bulbous, straight, pear, oval, funnel, serrated, triangular, rectangular, rounded or other. In addition, the nasal insert body can have a second portion having a shortened, slanted, curved, straight, funneled, concaved, pear, oval, serrated, triangular, rectangular, rounded or bulbous or other shape. The first portion can define a head having a bulbous, funnel, curved, a pear, oval, serrated, triangular, rectangular, rounded straight or other shape. The nasal insert inner surface can be more rigid than the outer surface. The nasal insert body can be used in the left or right nasal, or it can be configured to fit the left or right nasals, or it can have symmetrical features to be adapted to each side, or a universal fit. The nasal insert body can further have decorative elements as part of the nasal insert body or connected or attached thereto.

When inserting the nasal insert body, the nasal insert body can be compressed from one shape to another shape, whereby the nasal insert changes from one shape to another shape by manipulation or an external act. An applicator having a body including holding area and a gripping mechanism can be included. In a nasal insert apparatus combination, a nasal insert body having an inner surface defining an air passageway is combined with an applicator comprising a body having a gripping mechanism wherein the gripping mechanism of the applicator is connected to a gripping portion of the nasal insert body or to other part of the nasal insert body. The applicator is used in order to provide insertion and positioning of the nasal insert body and can be further used for applying material, pumping, or removal of the apparatus The present invention includes a method of diet, diet support, and diet compliment that can be combined with any diet effort whereby the eating experience of the user is flattened and impulse eating is reduced and eating in general is decreased. The steps of the method include providing an odor preventing nasal insert body for inserting into the nasal cavity wherein the nasal insert body comprises an inner surface defining an air passageway and an outer surface having a first portion and a second portion where the outer surface is adapted to form a seal between the nasal insert body and the nasal cavity. The user can insert the nasal insert body into the nasal cavity. Upon insertion, the seal is created between the nasal insert body and the nasal cavity. When the user breathes, the nasal insert body allows air only through the air passageway of the nasal insert body, thereby creating a bypass of the olfactory region and/or directing the air to bypass the olfactory region. The odors from the environment are thereby prevented from reaching the olfactory region of the user or a significantly smaller amount of environmental odor is reaching the olfactory region of the user and thereby reduces the sensation of food. Another effect that the nasal insert may have is delaying the effect of an external odor to the olfactory region. This will cause a delayed smelling effect on the user which in turn will inhibit the user's interest in food. Further, the method can include expanding the nasal insert body to fit within the nasal cavity. The expansion can be implemented by applying liquid to a nasal insert body, by using an applicator or in any other method. The nasal insert body or part of it rest within the inferior meatus of the nasal cavity or the middle and/or superior meatus of the nasal cavity. The nasal insert body can be used to provide drugs or medicine delivery to the user. The nasal insert body or part of it may further rest within the nasal vestibule of the nasal cavity. The nasal insert body can be used for anti-pollution or air purification to the respiratory system of the user. The method further can include using the nasal insert body to increase mucous secretion, which can then block, prevent, reduce or delay odors from olfactory region of the user.

When inserting the nasal insert body, the nasal insert body can be compressed from its initial shape or can be compressed in advanced, then expanded after it is inserted into the nasal cavity. The nasal insert body prevents or reduces odor from reaching the olfactory region of the nasal cavity. Alternatively, the nasal insert body can delay odor from reaching the olfactory region of the nasal cavity. An air lock can be formed inside the nasal cavity by using the nasal insert body and forming a pocket of air therein. When inserted fully into the nasal cavity, the nasal insert body can be undetectable from view outside the nose.

In different embodiments of the nasal insert body, the nasal insert body is either worn continuously for a period of time or can be placed in the nasal cavity and worn only during meals and when needed. It can be disposable or biodegradable as well. The nasal insert body can be inserted, compressed, expanded, or removed by the applicator.

BRIEF DESCRIPTION OF THE DRAWINGS

FIG. 2a is a side perspective view of a nasal insert made in accordance with the present invention;

FIG. 2b is a side perspective view of a nasal insert and application;

FIG. 5 is a side cross section of a nasal insert in accordance with the present invention;

FIG. 6a are side perspective view of 2 applicators made in accordance with the present invention;

FIG. 6b is a side perspective view of an applicator;

FIG. 7a is a cross section of a nasal insert and applicator made in accordance with the present invention;

FIG. 7b is a side perspective view of a nasal insert made in accordance with the present invention;

FIG. 8a is a side perspective view of a nasal insert showing a rectangular shaped nasal insert made in accordance with the present invention;

FIG. 8b is a rear perspective view of an L shaped tail of the nasal insert of FIG. 8a made in accordance with the present invention;

DESCRIPTION OF THE PRESENT INVENTION

Figure 3:
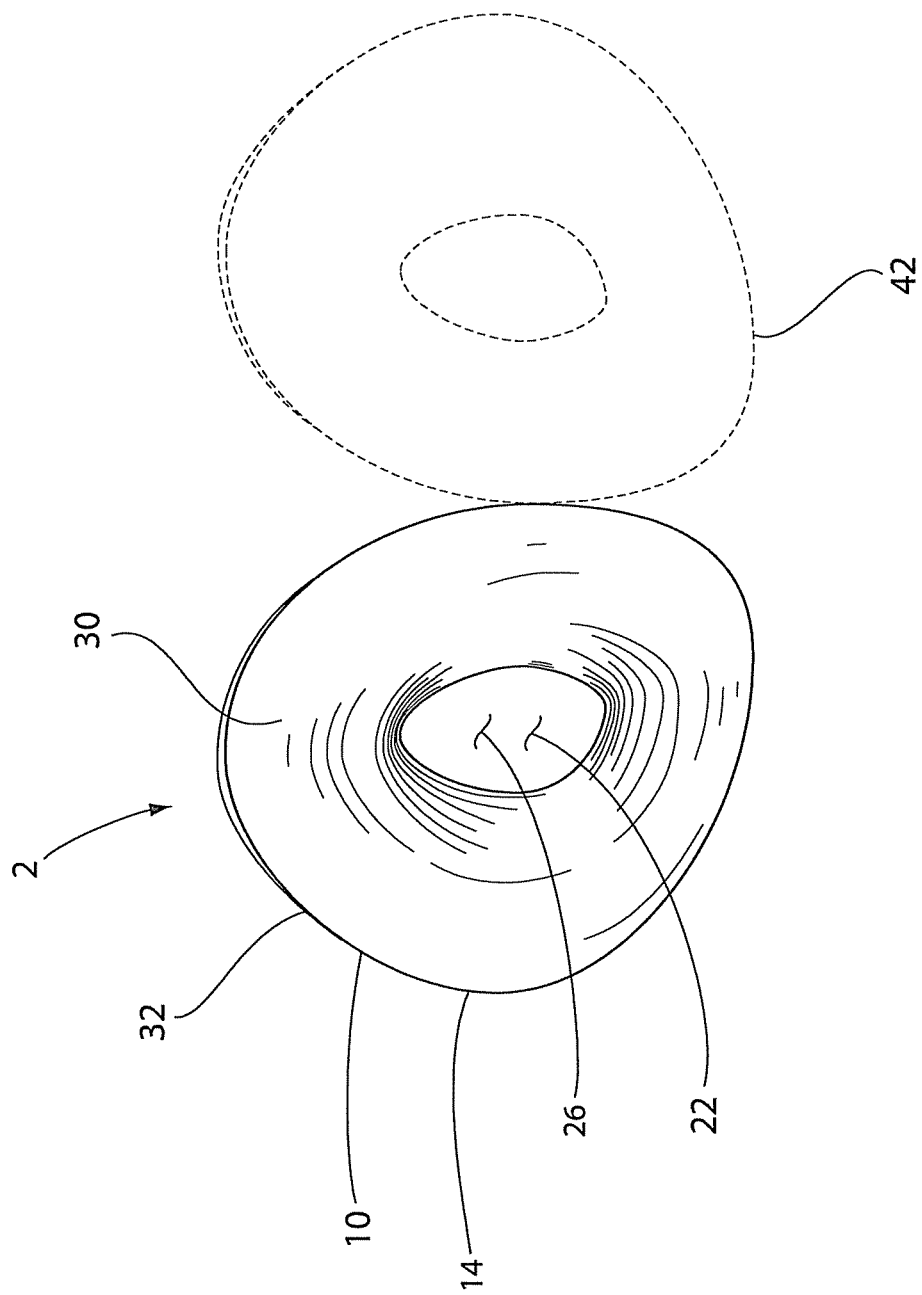
FIG. 3 is a front view of a nasal insert made in accordance with the present invention.
Figure 4:
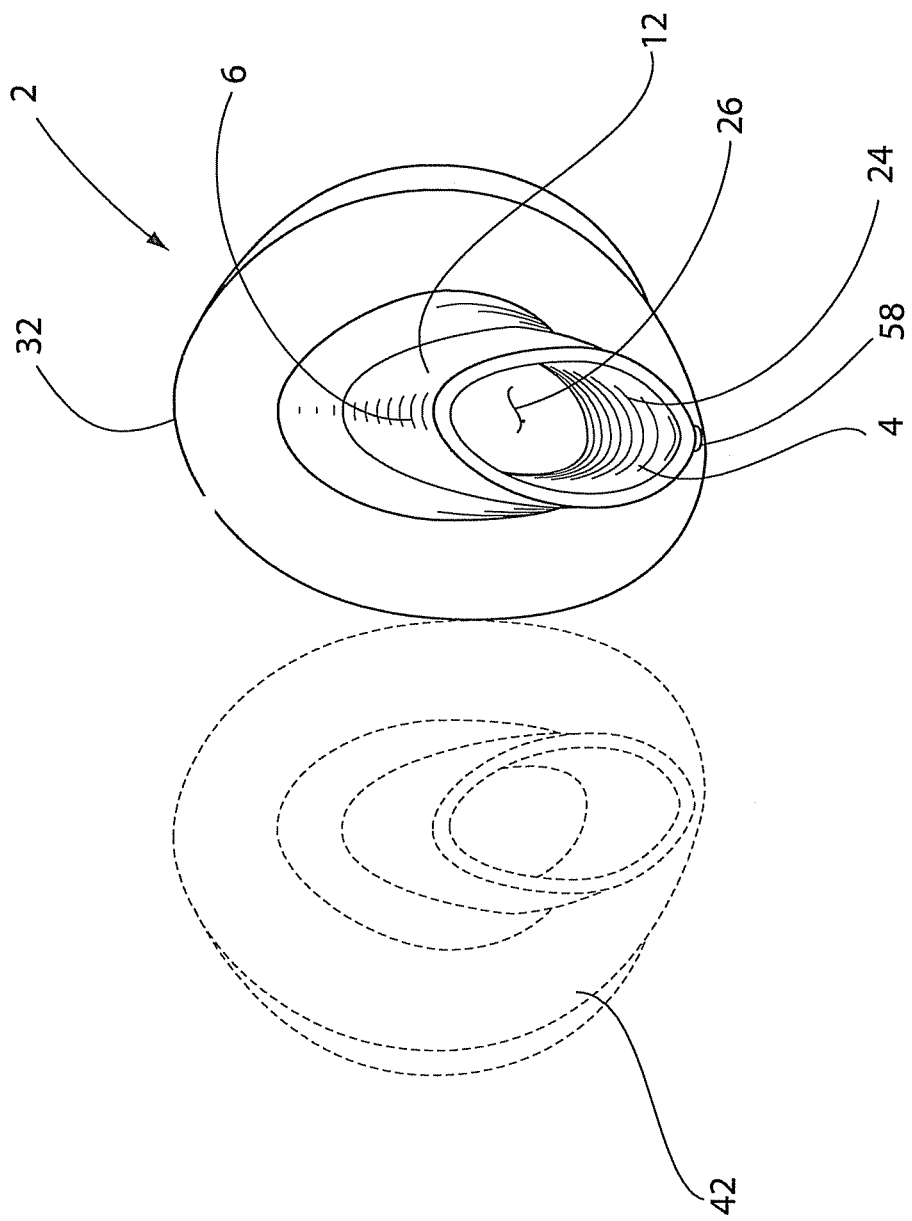
FIG. 4 is a rear view of a nasal insert made in accordance with the present invention.

With reference to FIGS. 2-4, a preferred embodiment of a nasal insert 2 of the present invention is shown. Nasal insert 2 is used to prevent odor or to significantly reduce odor particules to reach the olfactory region in the roof of the nasal cavity thereby stopping or decreasing smells and flavors of food. The nasal insert 2, includes a compressible body 8 having an inner surface 4 and an outer surface 6. The inner surface 4 of nasal insert body 8 defines an air passageway 26. The inner surface 4 forming air passageway 26 is rigid and yet flexible, enabling compression and expansion of air passageway 26 while always remembering and returning to its original shape to maintain an open air passageway. The nasal insert body 8 will get the shape of the nose cavity which can be a bit different from its original shape, for example, outside of the nose it can be oval, and in the nose it will be more bean like or smooth "L" shape. Also, the nose conchas are periodically expanding and shrinking and the nasal insert body 8, and accordingly the air passageway 26 are flexible enough to change their shape accordingly. Nasal insert body 8 will be rigid enough not to collapse and will maintain an open airway.

The ability of the nasal insert body 8 to compress and expand also minimizes the pressure against the nasal mucosa providing comfort. As shown in FIG. 3 with like numbers for like parts, the air passageway 26 begins at the upstream opening 22 and continuously extends through the nasal insert body 8 to the downstream opening 24, as shown in FIG. 4. Air passageway 26 extends throughout the entire length of the nasal insert body 8.

The nasal insert body 8 further includes a first portion 10 and a second portion 12. The first portion 10 includes an enlarged bulbous shaped head 14. The shape of the head 14 is non-limiting, as other shapes can also be used, such as for example, a pear, oval, funnel, curved, straight, triangular, rectangular, or rounded head. The first portion 10 may be flexible to adapt to the specific shape of the nasal cavity. The second portion 12 extends from the first portion 10 to the end 13 of the nasal insert body 8 and is substantially slightly curved cylindrical having a substantially oval shape. In addition, the second portion can include a tapered tail 20, shown in phantom. The second portion 12 may be flexible to adapt to the specific shape of the nasal cavity allowing maximal cross section area for air passageway and minimizing pressure over the nasal internal mucosa through the periodical expansion and reduction of the of the conches. The shape and size of the second portion 12 and of the tail are non-limiting and can vary as other shapes and sizes can be used having similar effects including round, bean, L shape, convex, straight, rectangular, curved, tapered, bulbous or others. Further, the second portion 12 can also have a slanted tail 18 or a bulbous shaped tail 37 similar to the head 14 as shown in FIG. 2b, forming a large bulbous tail for gently leaning against the nasal septum of the nasal cavity 100.

Figure 1:
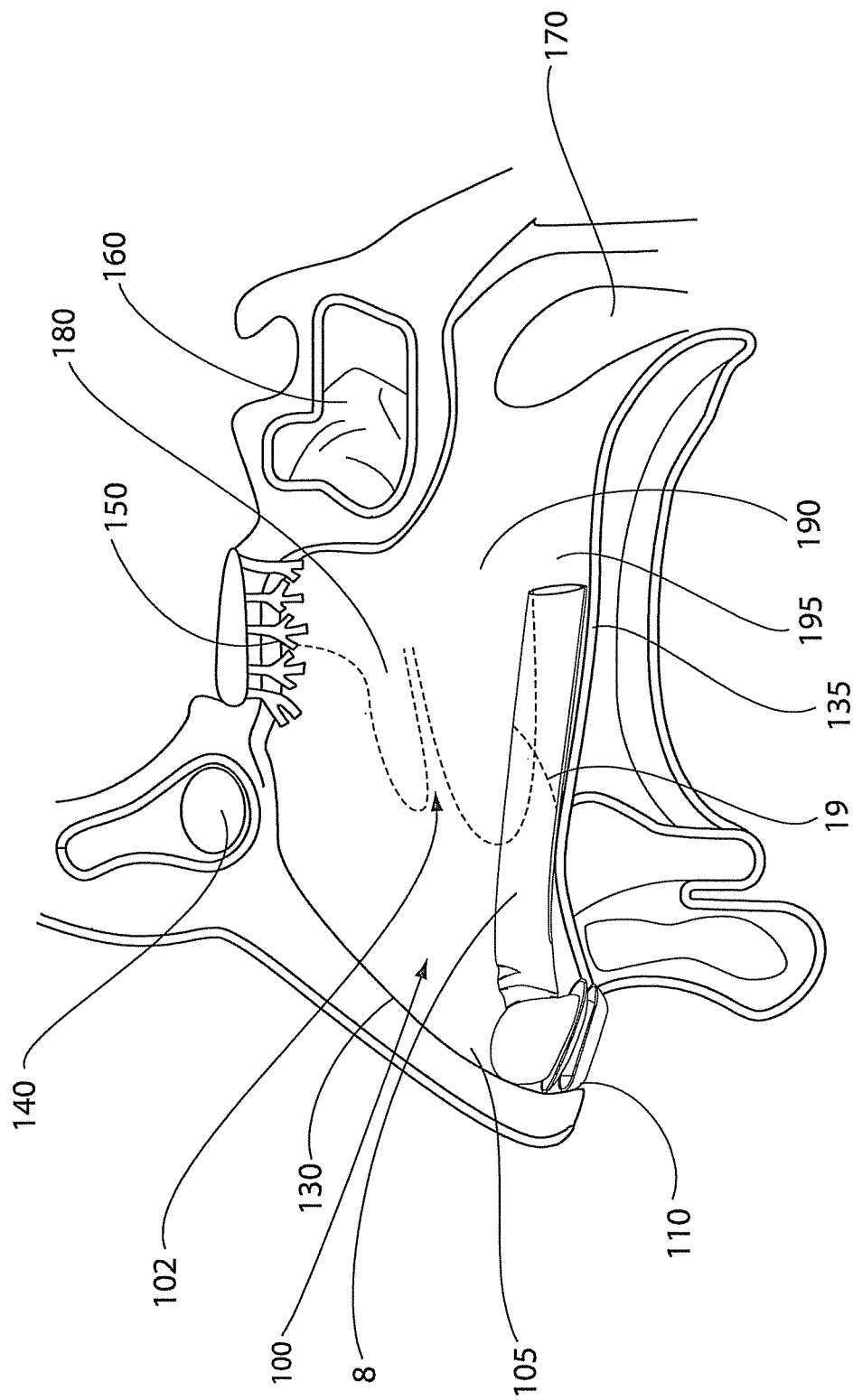
FIG. 1 is a cross section of a nasal passageway having a nasal insert made in accordance with the present invention.

When the nasal insert body 8 is inserted into the nasal cavity 100 as shown in FIG. 1, the nasal insert body 8 can be positioned inside the nasal vestibule 105 of the nasal cavity 100 forming a sealing between the nasal insert body 8 and the nasal walls, and allowing air to pass through air passageway 26 while blocking air from passing around it. By moving through air passageway 26 the air is conducted to the posterior nasal cavity bypassing the olfactory area 150 located in the uppermost part of the nasal cavity. Nasal insert body 8 can also have a shortened tail 19 (shown in phantom), in which case air is still bypassing the olfactory region 150 because it is directed past. Thus air passageway 26 of the nasal insert body 8 is preventing air from reaching an olfactory region 150 either by bypassing olfactory area 150 or by directing the air to bypass the olfactory area. The sense of smell originates in the nasal passageway. Odor particules stimulate the olfactory region 150 of the human nose. Nasal cavity 100 as shown in FIG. 1 includes a nostril 110, an upper nasal wall 130, a frontal sinus 140, and an olfactory region 150. The olfactory region 150 is covered by bipolar sensory neurons leaving the nose through the cribriform plate in the nasal roof synapsing in the olfactory bulb at the base of the frontal lobe of the brain. It is estimated that in the olfactory region 150, there are around six million sensory cells bilaterally. The olfactory senses reach the olfactory cortex in the rhinocephalon (not shown). Olfaction requires nasal air flow, which is part of respiration. The nasal cavities 100 further include nasal sinus 160 and nasopharynx 170. Also shown are the nasal conches 180, 190. The inferior meatus 195 is located between the inferior concha 190 and the nasal floor 135. During normal respiration, most of inhaled air runs through the inferior and middle meatuses 195,102 and only 10-15% of the inhaled air flows through the olfactory region 150 in the upper part of the nasal cavity 100, where odor is sensed. The specific route in which air goes into the nasal cavity 100 will determine which part of the air will come in contact with olfaction cells of the olfactory region 150. The air passageway 26 directs air to bypass the olfactory region 150 of the nasal cavity 100. By bypassing the olfactory region 150, odorous particulaes are prevented from reaching that olfactory region and by that effecting a persons flavor and impulse to eat.

To insert the nasal insert body 8 into the nasal cavity 100, the user can first compress the insert body 8 by squeezing it between fingers. In addition, an applicator can hold, squeeze, and assist navigating the nasal insert body 8 and aid prevent it from folding. The user can also, just push it in without compressing it at all.

Next, the user can then push the nasal insert body 8 into the nostril 110 and into the nasal cavity 100 to the inferior meatus meaning between the inferior turbinate and the nasal floor, the second portion 12 being placed first inside the nostril 110. As shown in FIG. 1, when the first portion 10 is inside the nasal cavity 100, the bulbous head 14 is positioned to form a seal of the nasal vestibule inside the nasal cavity 100. A seal is produced between the head 14 and the nasal vestibule in the nasal cavity 100 forcing air to move in and out only through the air passageway 26 that bypasses the olfactory region 150 or directs the air to bypass the olfactory region 150. The seal that is formed in the nasal vestibule is not meant to be limiting as it may be formed in other locations at the nasal cavity, for example: at the nasal valve, and serve the same function. Also the positioning at the inferior meatus is the preferred positioning but other locations may be used, for example: the middle meatus. The seal formed between the head 14 and the nasal cavity also enables the formation of an air lock inside the nasal cavity. By forming an air lock inside the nasal cavity 100, stagnant air blocks new air to enter and therefore air is stopped or reduced from circulating inside the nasal cavity 100. Exhaled air from the rear of the nasal cavity is blocked or delayed from entering by the stagnant air remaining in the nasal cavity. Air circulation is stopped or significantly restricted when the air lock is formed. Thus when an air lock is formed, it either prevents or significantly decreases odor from reaching the olfactory region 150 also during expirium. In addition, in case of a reduced but yet existing circulation, the air lock delays the arrival of odor to the olfactory area.

The nasal insert body 8 can be formed of one or more materials, and is primarily a soft, flexible and in some cases spongy body 8. The outer surface 6 of the nasal insert body 8 can serve the important purposes of absorbing mucous and facilitating the run-off of mucous. In addition the outer surface 6 or part of it can be used for forming a sealing between the nasal cavity 100 and the nasal insert 2 and for sealing the nasal insert itself, or to support drainage of the mucus backwards. In the first case when the outer surface 6 is used to absorb mucous, materials that are primarily absorbent can be used to form the outer surface 6 or part of it. Absorbent materials that can be used include for example cotton, hydro-gels, Merocell®, polyethylene glycol, types of polyurethane or polyvinyl chloride any type of suitable foam or any other suitable materials or combination of materials. The type of material is not meant to be limiting. A sealant material can also be used on the outer surface 6 of nasal insert 2 to seal the nasal insert 2, the sealant material can block odors and also facilitate mucous to run-off away from first end 11 toward a second end 13 of the nasal insert body 8 and into the nasal cavity 100. Materials suitable to form a strong seal can include silicon, Tygon®, any other plastic or combinations thereof or any other suitable materials. In the case of forming a seal between the nasal cavity and the nasal insert both absorbent or non absorbent materials can be used, for example: cotton, hydro-gels, Merocell®, polyethylene glycol, silicon, any type of polyurethane, polyvinyl chloride, Tygon® and other suitable materials. The outer surface 6 can be compressed or altered for smoother insertion gaining larger size after being placed in the nasal cavity. The inner surface 4, which forms the air passageway 26, can be made of a more rigid material that is also flexible and elastic in order to enable the air passageway 26 to expand and remember its original shape after it has been compressed or altered in some way. It may also enable insertion without folding in cases applicator is not used. Examples of suitable materials include silicon, Tygon®, types of plastic or any combinations or suitable material. Between the inner surface 4 and the outer surface 6, any number of additional layers can be included to form nasal insert body 8. Each layer of nasal insert body 8 materials can include spongy material, sealant material, absorbent material, anti bacterial material, alternative odor, anti pollutions, or medicine including but not limited to hydro-gels, silicone, Tygon®, cotton, Merocell®, silicon, polyurethanes, polyvinylchloride, dimethylpolysiloxan, silicic acid, azodiacarbonamide, reticulated foam, polyethers, polyesters, polysiloxanes, polycarbonate, polyolefins, polybutyrates, polyethylene teraphtalate (PET), Polymides, polyethylene glycol, activated carbon, biodegradable material, anti microbial agents, plastic materials, silver, bamboo, antimony, aluminum, metal materials, polymers, wood, resins, carbon based materials, carbon nanotubes (CNT), esters. Alternatively, air passageway 26 can be filled or partially filled with a porous material to absorb odors or for other uses, air can be allowed to pass through, and the porous material can trap or neutralize odorous particles. The inner surface 4 and the outer surface 6 as well as any layer between them can be partial layers or combinations of partial layers and full layers, and on the other hand they can be both made of the same material and be one layer as long as the structure and material support the characteristics of softness, rigidity, flexibility, and others as defined above and hereinafter. In lieu of a passageway, the nasal insert can be made entirely of a porous material. The rigidity and the softness of the inner and outer surface can be the same. In some embodiments the outer surface 6 can include a sealant material formed only on the head 14 of the first portion 10, the second portion can be made of absorbent material, with a sealing layer throughout the inner surface 4. The sealing layer of inner surface 4 can limit odor from penetrating the nasal insert body 8 and reaching the olfactory region 150, while the absorbent outer surface 6 reduces mucus and the sealant head 14 blocks air from flowing around the device and directs it. Alternatively, the nasal insert body 8 can be made of only one material, such as silicon, when the rigidity, softness, flexibility, resilience and other characteristics may be achieved by different thickness, stiffness, resilience, shape, grooves and other manageable parameters.

The nasal insert 2 can also be used to deliver odors. To deliver odor, the nasal insert body 8 can be made of natural materials or artificial materials such as esters which have inherent odor or that odor can be added to them. Alternatively, the materials of one or both of the inner and outer surface 4, 6 or any other layer of nasal insert body 8 can be impregnated with odorant particles or coated in order to deliver odor. Also odor can be applied to the relevant element by external tool such as applicator.

In addition, the nasal insert 2 can provide medication. In such a case, medicine can be coated on one or both of the inner and outer surface 4, 6 or on any other layer of the nasal insert 2, or can be applied to it through an external applicator. Alternatively, the materials of one or both of the inner and outer surface 4, 6 or any other layer of nasal insert body 8 can be impregnated with medicine or coated in order to deliver medicine. Also, antibacterial materials such as nanoscale silver or silver ion or bamboo or medicine can be used when making the composition of the nasal insert body 8 or coated thereon.

With reference to FIG. 2, nasal insert body 8 can include a flexible sealing member 30 in order to create a tight seal between the nasal insert body 8 and the nasal cavity 100. Sealing member 30 can be outward extending leaf from head 14 of the first portion 10 of the nasal insert 2. The sealing member 30 is a convex shaped leaf extending outward from the outer surface 6 of the head 14 of the first portion 10. The flexible yet rigid properties of sealing member 30 are adaptable to form a tight seal between the nasal insert body 8 and the nasal cavity 100 when the nasal insert body 8 is placed into the nasal cavity 100 *a*. The sealing member 30 has spring characteristics and also is positionable to provide a perfect match to the internal contour of the nasal cavity 100. The sealing member 30 can seal the nasal vestibule 105 and direct the inhaled air through the air passageway 26 of nasal insert 2. The sealing member 30 can provide an absolute seal and assure all nasally inhaled air will enter the air passageway 26 through the nasal insert 2. The sealing member 30 can also form an air lock after the nasal insert 2 is inserted into the nostril 110.

Multiple sealing members can be attached to the nasal insert body 8. As shown in FIG. 2, a second sealing member 32 can be placed on the head 14. The second sealing member 32 can be adjacent the first sealing member 30, extending outward from the outer surface 6 of nasal insert body 8. The second sealing member 32 combines with the first sealing member 30 to create better sealing and to better form an air lock after the nasal insert 2 is placed in the nostril 110. A third sealing member 34 (shown in phantom) can extend from the outer surface 6 of the second portion 12. A fourth sealing member 36 (shown in phantom) can extend along the second portion 12 of the nasal insert body 8. Additionally, as shown in FIG. 2b, nasal insert body 8 can have a bulbous tail 37 (shown in phantom) having an optional sealing member 38 thereon or different sealing members. The number and placement of sealing members is not meant to be limiting, as different combinations can be combined to create a desired airflow to block or prevent or reduce or delay odor from reaching the olfactory region.

A sealing member can also be formed of layered material on the nasal insert body 8. For example, the head 14 can have sealing material attached on its surface to define a sealing member of material. The sealing material can be shaped to provide characteristics of the sealing members. On the other hand it can be made with no additional layer or specific sealant member by suitable shape of the nasal insert body 8. In addition, any of the sealing members discussed can alternatively be partial sealing members as there is no requirement to completely surround the nasal insert body 8. The air lock can be formed in the upper nasal cavity.

With reference to FIG. 5, nasal insert body 8 is shown having an alternative sealing member 70. Sealing member 70 extends from head 14 and includes an inner surface 74 and an outer surface 72 forming a sealing member extending outward similarly to that of sealing member 30, however an inner surface 74 of sealing member 70 forms a groove 76 that may receive a ring member 78 or may alternatively receive a spring member (not shown), or remain empty. When a ring member 78 is inserted in groove 76, the sealing member 70 is stretched and strengthened and can form a tight seal between the sealing member 70 and the nasal cavity 100. The ring member 78 can be replaced when it becomes lose or if the nasal insert body 8 is to be removed. The outer surface 72 can be made from different material than the inner surface 74 or of the nasal insert head 14. The material can be absorbent or non absorbent. The cavity formed by the inner surface 74 is also a grip enabling the material of the outer surface 72 to be mechanically connected to the internal surface 74 and to the nasal insert head 14 in general. The outer surface may fully or partially surround the head and may also form different shapes (shown in phantom). The method and materials of sealing, sealing members and their connectivity to the nasal insert portions is not meant to be limiting as many different alternatives may be applied to perform the sealing. For example instead of having a bulge as a grip a niche, pin, or some adhesive material can be used (not shown).

Referring back to FIG. 2, a nasal insert body 8 may further include a flexible joint 40 defined by grooves 40' and 40" formed in the nasal insert body 8 and shown between the first portion 10 and second portion 12. The flexible joint 40 is formed by a groove or series of grooves defined through all or part of the layers comprising nasal insert body 8. The groove or series of grooves may be located between the first and second portions 10, 12 of the nasal insert body 8 or in other locations on the nasal insert body 8. The flexible joint 40 provides increased flexibility and can minimize the effect of movements of one nasal insert portion in regards to the other nasal insert portion to provide higher comfort. The increased flexibility can further minimize pressure against the nasal mucosa, the flexible joint 40 provides flexibility for the second portion 12 to bend with relation to first portion 10 in correspondence. Flexible joint 40 provides flexibility when navigating and inserting the nasal insert 2 into the nasal cavity 100. Still further, facial expressions which move the nose can be buffered in their effect on the nasal insert body 8 as the nasal insert 2 can flex at the flexible joint 40 to accommodate the movements. The flexible joint 40 is optional as embodiments with different joint or without high flexibility joint at all may serve as well.

FIG. 3 shows a right and left nasal insert 2, 42 (shown in phantom). When inserted into the nasal cavity, the nasal inserts 2, 42 can fit and be oriented for the left and right nasals respectively.

With reference to FIGS. 6, 6b and 7a, an applicator body 44 includes a holding region 46, a gripping mechanism 48 that may be comprise of forks or scissors-like arms or other suitable mechanism 50, 52 for gripping and/or squeezing the nasal insert body or for conducting other relevant activities such as applying material. The applicator 44 can be used to insert a nasal insert or for various other applications such as for example: removing the nasal insert, applying material, expending the nasal insert, pumping liquid, air or other material, or positioning a nasal insert. The flexibility of the nasal insert body 8 in general and along the second portion 12 in particular can enable both manually compressing of the nasal insert body 8 as well as compression with an applicator 44. In addition a flexible region 54 may be defined on the nasal insert body 8 enabling the collapsing through compression in a determined area and also providing higher comfort.

With reference to FIGS. 6a, 7a, and 7b, the applicator 44 may be connected to the nasal insert body 8, by having the forks 50, 52 of applicator body 44 gripping the gripping area of the nasal insert body. When the forks 50, 52 are pressed further onto the flexible region 54 of nasal insert body 8, or to other relevant area of nasal insert body 8, they create a squeezing action compressing the nasal insert body. Flexible region 54, or the other pressed part of nasal insert body 8, in turn, applies frictional resistance against the forks 50, 52, thereby retaining the applicator 44 until it is manually removed. Alternatively, FIG. 6b shows an applicator body 644 having scissor arms 650, 652 that can grip the gripping portion of the nasal insert body 8, or other part, and hold the nasal insert body squeezed using the flexibility and compressibility of the nasal insert shape and materials. The applicator in general may further include a stopper (not shown) preventing a too deep insertion of it into the nose for safety. In addition a stopper may also be added to stop the forks/scissors-like arms or other relevant part of an applicator from sliding off of the gripping portion of the nasal inset body 8 when they are connected. The applicator shape and the correlated method of gripping and compressing are not meant to be limiting as other methods and shapes may be applied. In addition the applicator may further allow reduced rigidity a long the nasal insert body 8 in general and along the air passageway 26 and the second portion 12 in particular, as the applicator will prevent the nasal insert from folding through insertion. Gripping portion such as 58 and/or flexible area such as 54 can be also applied to the first portion 10 of the nasal insert body 8, allowing smooth comfortable insertion of the head 14 as well. The use or the presence of an applicator is not meant to be limiting as many embodiment with no applicator can serve as well. Also the presence of a dedicated flexible area is optional as the nasal insert body can flex without it. For example, the nasal inserts shown in FIGS. 2a and 2b has a gripping portion 58, but don't have the flexible area 54.

FIG. 7b shows a compressed nasal insert body 8 with an applicator body 44 connected.

Alternatively, the forks/scissors-like arms or other relevant mechanism may grip the gripping portion of the nasal insert body 8 and hold the nasal insert body squeezed using the flexibility and compressibility of the nasal insert shape and materials or by causing a collapsing in a different designated flexible area along the nasal insert body 8. A gripping region 58 of the nasal insert body 8 may further act as a guide for insertion. The shape of the gripping portion 58 is not meant to be limiting as other shapes can be applied for the same purpose, for example the gripping portion such as shown in FIGS. 2a and 2b. When the applicator 44 is connected to the nasal insert 2, the forks 50, 52 may hold the nasal insert squeezed. The use of forks or scissors-like arms or other relevant mechanism for gripping the nasal insert body 8 or for squeezing and expanding it or for any other use of the applicator is not meant to be limiting as many other mechanisms may perform. The nasal insert body 8 may further include a gripping area. With reference to FIG. 7a, the gripping area 58 will be held by an applicator 44. The applicator 44 may also squeeze the nasal insert body 8 allowing the nasal insert body 8 to pass easily into the nasal cavity 100. The forks 50, 52 are retained on the gripping area of the nasal insert body by a combination of restive pressure and the whole gripping region 58 and will remain in place until the user pulls the applicator 44 out from the nasal insert 2. The applicator shape and the correlated method of gripping and compressing are not meant to be limiting as other methods and shapes may be applied.

The applicator 44 can navigate the nasal insert 2 into the nasal cavity 100 and can also be used to adjust the nasal insert 2 inside the nasal cavity 100. In addition, the applicator 44 can compress and open the nasal insert 2 when inserting and also removing the nasal insert 2. Nasal inserts can be offered with or without applicator. Applicator 44 can be made of a rigid and sturdy but yet elastic material such as plastic, metal, and rigid silicon. The applicator 44 can be more rigid than the nasal insert 2 thereby allowing the nasal insert 2 to be navigated by the applicator 44. The type of material is non-limiting, as other materials can be used to make the applicator 44.

Additional embodiments are shown in FIGS. 8a, 8b, 9, 10, and 11. FIG. 8a shows an embodiment of a nasal insert 202 having an enlarged rounded rectangular shaped head 214 in a first portion 210 and an L-shaped tail 216 in a second portion 212. The enlarged rounded rectangular shaped head 214 is surrounded with a bulge 220 that can be used as a grip for another layer or as a sealing member or as a groove for a spring and can also provide flexibility inside the nasal cavity 100 to expand into the nasal cavity 100 forming a tight seal within. An optional layer 218 can be made of absorbent or non absorbent material providing better sealing and higher comfort and can fully or partially cover the walls of the head 214. With reference to FIG. 8b, the tail 216 of nasal insert 202 is formed of an L shape and forms an L-shaped air passageway 226 there through. The "L" shape suits the internal natural nasal cavity shape.

Figure 9:
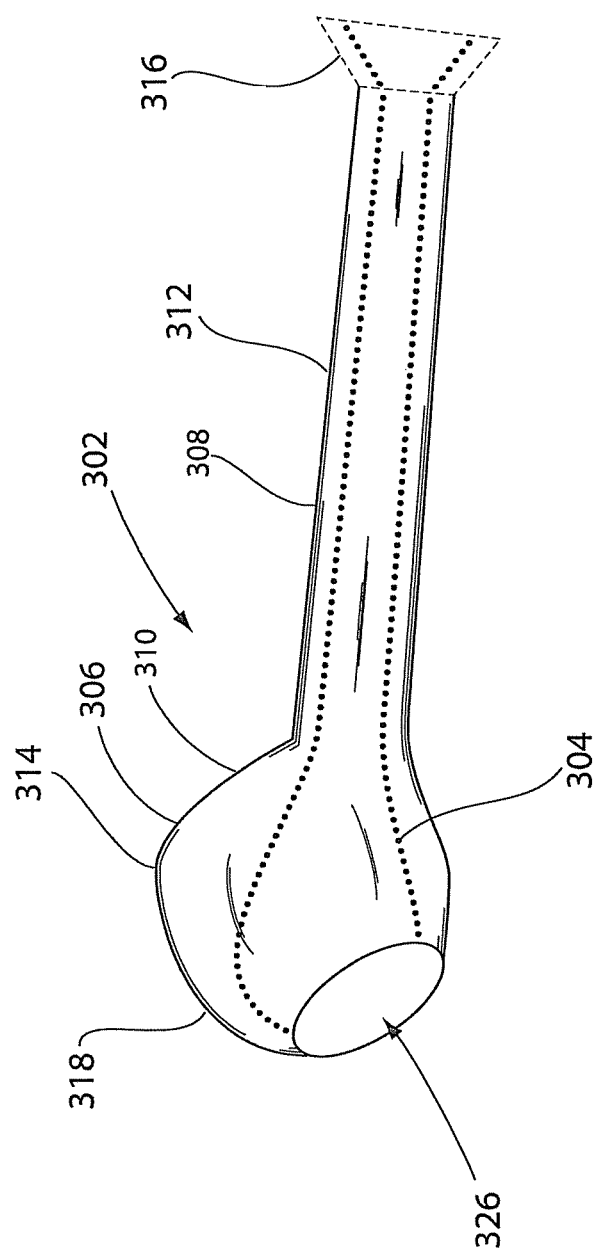
FIG. 9 is a side view of a nasal insert having a bulbous head and a flared second end shown in phantom made in accordance with the present invention.

FIG. 9 shows a flexible nasal insert 302 having a wider bulbous round head 314 in a first portion 310 and a thinner second portion 312. The air passageway 326 has a wider air passageway in the first portion 310 and it narrows through the second portion 312. The outer soft surface can be made of absorbent or non-absorbent compressible or non compressible material, and the inner surface more rigid but elastic. Also the inner layer can be made of sealed material preventing odor particles from moving through it. The air passageway 326 enables easier movement of air through the nasal insert 302. The nasal insert 302 can be positioned in nasal cavity and the head 314 will form snug fit with nasal vestibule 105 internal walls and block the air from flowing around the head directing it into the air passageway 326. The air passageway 326 may by pass the olfactory area or direct the air to bypass the olfactory area.

Alternatively, the surface 318 or the whole outer surface 306 of the nasal insert 302 can be made of a high density sealing material or an additional layer of high density sealing material can be placed on a first layer of spongy or porous material or the outer surface covering it fully or partially. The high density material can prevent any inhaled or exhaled air from reaching the olfactory region 350 of the nasal cavity 300 and contributes for good drainage of the mucus.

Alternatively, air passageway 326 can be fully or partially filled with material or the whole device is made of porous material. In this case the nasal insert body 308 can be fully or partially covered with a sealing layer.

With continuing reference to FIG. 9, the length of the nasal insert 302 can be varied by increasing and decreasing the length of the second portion 312. The nasal insert 302 can also include a tail 316 (shown in phantom). Tail 316 directs the exhaled air to move out more easily through the pipe and directs it into the air passageway by bypassing the olfactory region 150. It also supports the formation of airlock in sturdier manner and contributes to preventing or significantly reducing odor reaching the olfactory area.

Figure 10:
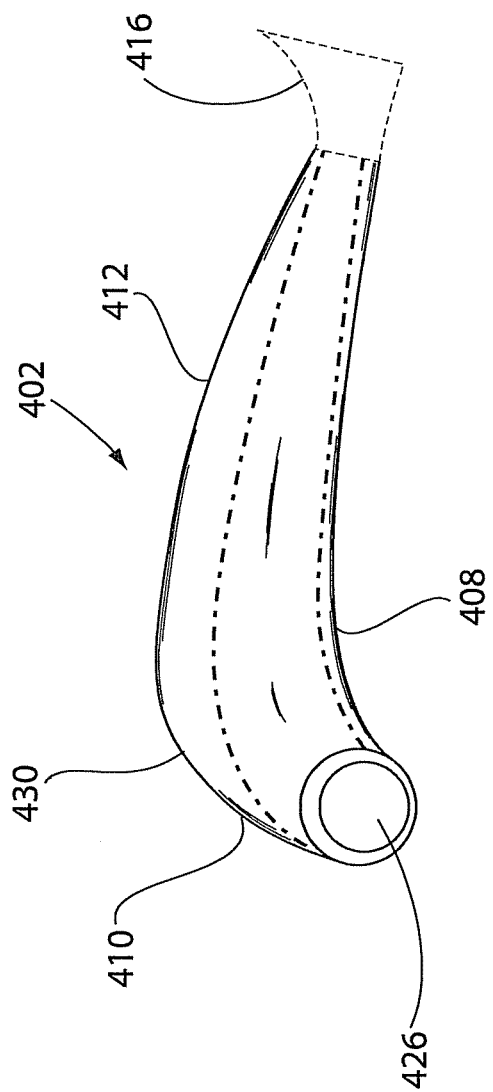
FIG. 10 is a side view of a nasal insert made in accordance with the present invention.

FIG. 10 shows a nasal insert 402 having an alternative convex shape. Nasal insert 402 having a first portion 410 includes a curved body 408 and curved air passageway 426 there through. The curve of nasal insert body 408 can fit nasal cavity 100. The region between the first portion 410 and second portion 412 can use layered material to form a sealing member 430 that can press against the nasal cavity 100 forming a tight seal. A tail 416 (shown in phantom) can be included having a wider air passageway in the second portion 412 to aid respiration and direct exhaled air into the air passageway more easily, and to better form the airlock that assist in preventing odor from reaching the olfactory area.

Figure 11:
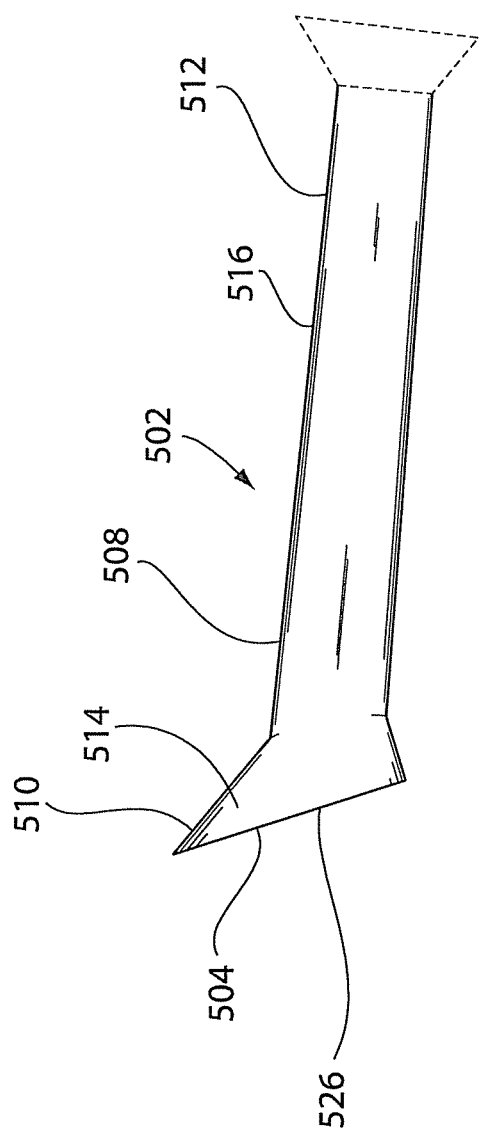
FIG. 11 is a side view showing a nasal insert having a flared head made in accordance with the present invention.

FIG. 11 shows a nasal insert 502 having a first portion 510 and a second portion 512 having a flared head 514 and a tail 516. The inner surface 504 defines an air passageway 526 through the nasal insert 502. The air passageway 526 can remain constant, decrease, or increase in width or can change in shape. The tail 516 can decreases in width or remain constant or increase from the first portion 510 to the second portion 512. The length of the tail can vary and the shape of it as well, for example the fact that it has flared or non flared tail or oblique on other.

The present invention also provides a method for using the nasal insert for diet purposes to flatten the eating experience and to reduce eating consumption. First, a nasal insert 2, as shown in FIG. 2, is provided having an air passageway 26. The nasal insert 2 is inserted into the nostril 110 and into the nasal cavity 100. The nasal insert 2 can be inserted as previously described hereinabove by pressing the nasal insert body 8 between two fingers of the hand, or by using an applicator or in any other suitable manner or it can be compressed in the first place. The user can lift the hand with the nasal insert 2 up toward the nose and under the nostril 110. The user then pushes the nasal insert body 8 in and into the nasal cavity and one nasal insert can be inserted through each of a right and left nostrils and directed into the nostril 110 with the user's fingers or by using an applicator. Using fingers or an applicator, the adjustment of the nasal insert 2 can be made. The user can position the nasal insert body 8 to fit snuggly inside the nasal cavity 100. In alternative embodiments, a premolded liquid or body temperature activated or other relevant method for example premolded with an applicator, insert can be provided, which can be inserted into the nose and pushed inside the nasal cavity. Once inside, the mucous and bodily fluids or external dropping of liquid or body temperature or other relevant act such as for example manually turning or opening the applicator, can activate the premolded nasal insert 2 to decompress inside the nasal cavity 100 and expand into the nasal cavity 100 forming a tight but comfortable fit. The premolded nasal insert 2 can also be activated using an applicator 44 having liquid thereon which can be placed on the nasal insert body 8, or applying some other act on it. Once inside the nasal cavity 100, the head 14 of the nasal insert 2 can stretch and form a comfortable fit and also block inhaled air from passing around the nasal insert 2 and thereby directing the inhaled air to pass in through the air passageway 26. Sealing members 30, 32, 34, 36, 38 of FIG. 2 or others, can also aid in forming a seal and also block air thereby directing the air through the nasal insert air passageway and/or forming an air lock in nasal cavity 100. When the user begins breathing after inserting the nasal insert body 8, the inhaled air is directed into the air passageway 26 and through the nasal insert body 8 to the respiratory passes of the user. Exhaled air is also directed into the air passageway 26 and out through the head 14 of the nasal insert body 8. This direction of air creates a bypass of olfactory region 150 and in doing so prevents or significantly reduces or delays odors from reaching the olfactory region 150. By preventing the odors from the olfactory region 150, any odor from food is also prevented thereby flattening the eating experience by lessening the sensation of food and reducing the impulse eating. Incase of delayed smelling also impulse eating and flattening of the eating experience together is achieved as the smelling is not timely coordinated with the availability of the desired food. Alternative embodiments, as described hereinabove, can be inserted similarly.

To remove the nasal insert 2, the user can push air sharply while wiping the nose, by sneezing very strongly, or snorting outward through the nasal cavity 100 causing the nasal insert 2 to fall forward through a nostril 110 from where it can be pulled completely out of a nasal cavity 100. It can also be removed by pushing it out through the nose be gently squeezing the lower part of the nose from outside or by inserting finger to the nasal vestibule and pulling it out. Further, the nasal insert 2 can be pulled out using an applicator 44. Still further, threads can be attached to the nasal insert body 8 for pulling the nasal insert 2 out of the nasal cavity 100. Alternative inserts of varying shapes and sizes, as described hereinabove, can be removed in a similar method.

Once the nasal insert body 8 has been used, the user can either clean the nasal insert body 8 and use it again or can dispose of the nasal insert body 8 depending of the specific material and embodiment and of other parameters such as for example: medical instructions of use. One indication that the nasal insert body 8 should be replaced is mucosal saturation on the nasal insert body 8 in case of absorbent material. The nasal insert can be used continuously for a period of time, subject to the relevant limitations such as materials, medical, supporting diet instructions and others. Instructions can be provided defining a period of time the nasal insert body 8 can be used, for example, a period of several hours before removing to allow the nasal mucosa to rest. Alternatively, the nasal insert body 8 can be used only when the user is around food or is close to odorous or going to a meal or is eating. The nasal insert body 8 can be made in long lasting format and reusable, or alternatively it can be made in disposable format allowing one or only few uses before disposing In an alternative disposable model, biodegradable materials can be used to make the nasal insert body 8.

When the nasal insert body 8 is inserted inside the nostril 110, the nasal insert 2 can be worn without or almost without visual detection from the outside the nose. Alternatively, the nasal insert 2 can include decorative elements such as attachments such as nose rings and jewelry (not shown) or the nasal insert 2 can be colored and extend beyond the nostril up to the outer side of the nose and/or down towards the mouth or towards the septum and the middle of the nose.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

The claimed invention is:

1. An odor preventing nasal insert for insertion into a nasal cavity, said nasal insert comprising a body having an inner surface, defining an air passageway, and an outer surface, having a first portion and a second portion, said outer surface of said nasal insert body configured to form a seal between said nasal insert body and the nasal cavity and said nasal insert body extending into the nasal cavity beyond the nasal valve and resting against a portion of the nasal cavity, wherein the nasal insert body bypasses or directs air to bypass the olfactory region, and wherein said nasal insert body is configured to be fully located in the nasal cavity.

2. The nasal insert as in claim 1, further comprising a sealing member extending from said outer surface of said nasal insert body, wherein said sealing member is adapted to the nasal cavity.

3. The nasal insert of claim 2, wherein said sealing member is a sealing material or layer of material.

4. The nasal insert of claim 1, wherein said nasal insert body comprises additional full or partial layer or layers between said inner surface and said outer surface of said nasal insert body.

5. The nasal insert as in claim 1, wherein said body can comprise absorbing material adapted to absorb fluids.

6. The nasal insert as in claim 1, wherein the outer surface is adapted to support mucus drainage.

7. The nasal insert as in claim 2, wherein said sealing member is located on the nasal insert body adjacent said first portion of said nasal insert body, adjacent the conjunction of first portion and second portion of said nasal insert body, or at the second portion of said nasal insert body.

8. The nasal insert as in claim 1, wherein the inner surface defining an air passageway is more rigid than the outer surface.

9. The nasal insert as in claim 1, wherein said nasal insert body further comprises a gripping portion.

10. The nasal insert as in claim 1, wherein said nasal insert body is adapted to flexibly compress and expand.

11. The nasal insert as claimed in claim 1, wherein said nasal insert body further comprises a flexible joint.

12. The nasal insert as in claim 1, wherein the air passageway of said nasal insert body includes a filling material.

13. The nasal insert of claim 12, wherein said filling material reduces the amount of air moving through nose while breathing.

14. The nasal insert as in claim 1, wherein the nasal insert further comprises:
an odor;
an anti-bacterial material;
oily or watery material; and/or
medication.

15. The nasal insert as in claim 1, wherein said inner surface or outer surface includes a first end and a second end, wherein one end is wider than the other end.

16. The nasal insert as in claim 1, wherein said body is configured to fit one of a left side and/or a right side nasal cavity.

17. The nasal insert as in claim 1, wherein said nasal insert body further comprises a decorative element.

18. The nasal insert as in claim 1, wherein said nasal insert body further comprises different shapes, whereby said nasal insert changes from one shape to another shape via manipulation or an external act.

19. The nasal insert as in claim 1, wherein said nasal insert body extends into the nasal cavity an amount sufficient to minimize the amount of odor contacting the olfactory region of the nasal cavity.

20. The nasal insert as in claim 17, wherein at least a portion of said decorative element extends outside the nasal cavity.

21. The nasal insert as in claim 1, wherein the nasal insert is configured to be held and secured within the nasal cavity solely by cooperation of the outer surface of the insert with the nasal cavity.

22. A nasal insert apparatus comprising in combination:
an odor preventing nasal insert for insertion to into a nasal cavity, said nasal insert comprising a body having an inner surface defining an air passageway, and an outer surface, having a first portion and a second portion, said outer surface of said nasal insert body configured to form a seal between said nasal insert body and the nasal cavity and said nasal insert body extending into the nasal cavity beyond the nasal valve and resting against a portion of the nasal cavity, wherein the nasal insert body bypasses or directs air to bypass the olfactory region, and wherein said nasal insert body is configured to be fully located in the nasal cavity; and
an applicator comprising a body, having a gripping mechanism, wherein said gripping mechanism is configured for insertion within the nasal cavity and is connected to said nasal insert body, whereby said applicator can insert and position said nasal insert body into said nasal cavity.

23. The nasal insert apparatus of claim 22, wherein the applicator is configured for insertion within the air passageway of the nasal insert body.

24. The nasal insert apparatus as in claim 22, wherein the nasal insert is configured to be held and secured within the nasal cavity solely by cooperation of the outer surface of the insert with the nasal cavity.

25. A method for dieting, diet support, and diet complementing method for flattening an eating experience and/or reducing impulse eating, to reduce eating, comprising the steps of:
providing an odor preventing nasal insert body for insertion into a nasal cavity, said nasal insert body comprising an inner surface, defining an air passageway, and an outer surface having a first portion and a second portion, said outer surface adapted to form a seal between said nasal insert body and the nasal cavity;
inserting said nasal insert body into the nasal cavity such that the nasal insert body extends into and rests against a portion of the nasal cavity wherein said nasal insert body is configured to be fully located in the nasal cavity;
creating a seal between said nasal insert and the nasal cavity in the nasal cavity;
breathing through the nose, wherein the nasal insert body of said nasal insert is creating a bypass of the olfactory region or directing the air to bypass the olfactory region; and
preventing or reducing environmental odor from the olfactory region.

26. The method of claim 25, further including the step of expanding the nasal insert body to fit within the nasal cavity.

27. The method of claim 25, further comprising the step of applying a material to the nasal insert body.

28. The method of claim 25, wherein said nasal insert body or part of said nasal insert body rests within the inferior meatus of the nasal cavity.

29. The method of claim 25, wherein said nasal insert body or part of said nasal insert body rests within the nasal vestibule of the nasal cavity.

30. The method of claim 25, wherein said nasal insert body or part of said nasal insert body rests within the middle and/or superior meatus of the nasal cavity.

31. The method of claim 25, wherein said nasal insert body is used for drug or medicine delivery.

32. The method of claim 25, further including using said nasal insert body for anti-pollution or air purification.

33. The method of claim 25, further including said nasal insert to increase mucus secretions to block, or prevent, or reduce, or delay smelling.

34. The method of claim 25, further comprising the steps of compressing the nasal insert body prior to inserting the nasal insert body; and/or
expanding the nasal insert body after insertion in the nasal cavity.

35. The method of claim 25, wherein said nasal insert delays odor reaching the olfactory region of the nasal cavity.

36. The method of claim 25, wherein said sealing member and/or other nasal insert body part forms an airlock in the nasal cavity.

37. The method of claim 25, further comprising the further step of placing the nasal insert body inside the nose undetectable from view outside the nose.

38. The method of claim 25, wherein said nasal insert is worn continuously for a period of time.

39. The method of claim 25, wherein said nasal insert is worn while eating and /or wherein a wearer is in an environment of food.

40. The method of claim 25, wherein said nasal insert is inserted, compressed, expanded, or removed by an applicator.

41. An odor preventing nasal insert for insertion into a nasal cavity, said nasal insert comprising a body having an inner surface defining an air passageway, and an outer surface, the nasal insert body configured for extending into the nasal cavity beyond the nasal valve and being held in place by the nasal cavity for delaying or blocking odor from reaching the olfactory region of the nasal cavity and/or for reducing the amount of odor reaching the olfactory region.

42. The odor preventing insert of claim 41, wherein the nasal insert is configured to be held and secured within the nasal cavity solely by cooperation of the outer surface of the insert with the nasal cavity.

43. An odor preventing nasal insert configured for insertion into a nasal cavity for dieting, diet support, and diet complementing for flattening an eating experience and/or reducing impulse eating to reduce eating and/or reducing an impulse to eat to support dieting, said nasal insert comprising an odor preventing nasal insert body adapted for insertion into a nasal cavity beyond the nasal valve, said nasal insert body comprising an inner surface, defining an air passageway, and an outer surface, having a first portion and a second portion, and wherein upon insertion into the nasal cavity, outer surface of said nasal insert body is configured to form a seal between said nasal insert body and the nasal cavity while allowing the user to breathe through the nose, said nasal insert configured to create a bypass of or to direct the air to bypass the olfactory region to prevent or reduce odor from reaching the olfactory region and thereby reducing one's impulse to eat.

44. The odor preventing nasal insert of claim 43, wherein the nasal insert is configured to be held and secured within the nasal cavity solely by cooperation of the outer surface of the insert with the nasal cavity.

* * * * *

UNITED STATES PATENT AND TRADEMARK OFFICE
CERTIFICATE OF CORRECTION

PATENT NO. : 8,517,026 B2  
APPLICATION NO. : 12/390893  
DATED : August 27, 2013  
INVENTOR(S) : Adva Beck Arnon Page 1 of 1

It is certified that error appears in the above-identified patent and that said Letters Patent is hereby corrected as shown below:

Title Page, Item (12) "AMON" should read -- ARNON --.

Title Page, Item (76) Inventor, "ADVA BECK AMON" should read -- ADVA BECK ARNON --.

Signed and Sealed this  
Twenty-ninth Day of October, 2013

Teresa Stanek Rea  
*Deputy Director of the United States Patent and Trademark Office*